United States Patent [19]

Tchen et al.

[11] Patent Number: 4,810,644

[45] Date of Patent: Mar. 7, 1989

[54] PROBE AND A PROCESS FOR THE DETECTION OF SPECIFIC MICROORGANISMS, PARTICULARLY LEGIONELLAS, IN ENVIRONMENTS WHICH CONTAIN THEM

[75] Inventors: Paul Tchen, Nanterre; Nicole Desplaces, Paris; Patrick Grimont, Paris; Francine (maiden name Besse) Grimont, Paris, all of France

[73] Assignees: Institut Pasteur; Institut National de la Sante et de la Recherche Medicale, both of Paris, France

[21] Appl. No.: 762,053

[22] Filed: Aug. 2, 1985

[30] Foreign Application Priority Data

Aug. 2, 1984 [FR] France ............................... 84 12250

[51] Int. Cl.$^4$ ..................... C12P 19/34; C07H 19/06; C07H 15/12
[52] U.S. Cl. ........................................ 435/91; 536/26; 536/27; 536/28; 935/77; 935/78
[58] Field of Search ................. 435/6, 91; 436/501; 536/27, 28, 29, 26; 935/77-78

[56] References Cited

U.S. PATENT DOCUMENTS 4,358,535 11/1982 Falkow et al. .................. 435/36 X

FOREIGN PATENT DOCUMENTS 0120658 3/1984 European Pat. Off. .
0133288 7/1984 European Pat. Off. .
8402721 1/1984 World Int. Prop. O. .

OTHER PUBLICATIONS van Ketel et al., *Journ. Clin. Microbiol*, 20 No. 3: 362-364 (1984).
Tompkins, L., *Clinics in Laboratory Medicine*, 5 No: 99-107, (1985).
Patamaroj, V. et al., *Journ. Clin. Microbiol*, 18, No. 6: 1429-1431 (1983).
Starr, M. et al., in "The Prokaryotes" vol. 1, (Stan et al. eds) Springer-Verlay Publishers pp. 3-42 (1981).
J. Ludwig et al., *Chemical Abstracts*, vol. 99, no. 15, p. 350, No. 118946k (Oct. 1983) & *Arch. Microbiol.*, 135(1), pp. 45-50 (1983).
R. J. Van Ketel et al., *Chemical Abstracts*, vol. 101, No. 17, p. 363, No. 147436j (Oct. 22, 1984).
S. E. Hoffner et al., *Chemical Abstracts*, vol. 101, No. 15, p. 360, No. 126407k (Oct. 8, 1984) & *Inst. Natl. Sante Rech. Med.* (colloq.), 114, pp. 383-391 (1983).

*Primary Examiner*—Robert J. Warden
*Assistant Examiner*—Jack Spiegel Jr.
*Attorney, Agent, or Firm*—Finnegan, Henderson, Farabow, Garrett & Dunner

[57] ABSTRACT

The invention concerns a composition of fragments of DNA utilizable as a probe for the detection of specific micoorganism, notably Legionella, in environments which contain them. These compositions are obtained from the whole genomes of the microorganisms to be detected, after fragmentation of these genomes, particularly by using a restriction enzyme, and eliminating those sequences of the genomic DNA which are susceptible to being transcribed to ribosomal RNA.

21 Claims, No Drawings

PROBE AND A PROCESS FOR THE DETECTION OF SPECIFIC MICROORGANISMS, PARTICULARLY LEGIONELLAS, IN ENVIRONMENTS WHICH CONTAIN THEM

*Legionella pneumophila* (L.P.), responsible for Legionnaire's Disease (L.D.), was clinically individualized during the summer or 1976. It is the principal agent of legionelloses. The term "legionellosis" is used to name the infections caused by the Legionellaceae. All these bacteria, but especially L.P. have been demonstrated in a great number of samplings of water taken from lakes, cooling towers and principally from water distribution systems - these latter two being at the origin of sporadic and epidemic cases of Legionnaire's Disease in Europe as well as in North America.

The taxonomic and phenotypic characteristics of the Legionellaceae are well known. They are described by Brenner, D. J., Feeley, J. C. and Weaver, R. E. in Bergey's Manual of Systematic Bacteriology, Vol.I, 1984, Williams and Wilkins, Ed., Baltimore/London.

The characteristics which these bacteria have in common are: the fact that they are Gram negative, obligate aerobe bacilli; they have complex nutritional reguirements for their culture in the laboratoryprincipally being dependent upon L-cysteine HCl and on ferric salts; they are weekly oxidase positive; do not reduce nitrates; are urease negative; and liquify gelatin; their cell walls include branched fatty acid chains.

Among the Legionellaceae, the species designated as *Legionella pneumophila* presents the same phenotypic characteristics of the Legionellaceae. The identification of the species lies in the use first of polyvalent anti-Legionella specific fluorescent immuno-serums (8 serotypes currently available) then monovalent, by direct immunofluorescence.

The in vitro diagnosis of L.D. as it is currently practiced rests on the demonstration of Legionella in culture, or by a significant increase in the level of its antibodies. The search for Legionella by culturing pathological material (pulmonary tissue, tracheal exudates, expectoration, pleural fluid, blood, etc.) is delicate and requires special gel culture media known as "Buffered Charcoal Yeast Extract" (BCYE), which, apart from charcoal and yeast extract, contains ferric pyrophosphate and L-cysteine HCl, as described by Pasculle, A.W. and Coll., J. Infect. Dis., 1980, 141, 727–732, rendered partially selective by the addition of antibiotics, for example such as described by Edelstein. P. H.,J. Clin. Microbiol., 1981, 14, 298–303. This search also implies prior or simultaneous decontaminating operations:treatment by heat at 60° C. for 1 to 2 minutes, or by buffered acid at pH 2.2 for 10 minutes. Such treatments, which are intended to reinforce the selectivity of the diagnostic tests, have the concomitant disadvanteage of reducing the quantity of Legionella in any material so treated. Besides, the growth of *L. pneumophila* is slow and the first colonies only appear 2 to 4 days after cultivation. The identification of these colonies hinges on criteria related to the culture conditions (dependency on *L. cysteine*) or on biochemical or antigenic characteristics: these latter are detected by direct immunofluorescence using the specific anti-serums of each serogroup of *L. pneumophila*.

These searches, already long and fastidious when applied to pathological material likely to contain relatively high concentrations of L.P., become practically impossible when applied to the study or surveillance of contaminations or of the pollution of circulating waters or to environmental monitoring generally. The slowness of the growth of legionellas, the presence of other, faster growing, contaminating microorganisms, and the difficulty of developing media which are genuinely selective all render routine monitoring particularly problematic. Add to these the diversity which may be observed in the immunological properties of the different species of legionellas.

The use of techniques relying on the hybridization of a particular cloned nucleotide sequence, especially of a cloned chromosomic gene, with the genome (first rendered accessible to hybridization) of the microorganisms being sought, could in no way initially be considered. One first reason for this was the fact that sufficiently specific DNA sequences are not at present available to offer a reasonable certainty that the hybridization would be really selective. This non-selectivity risked being all the more pronounced as the organization of the genomic chromosomes could vary greatly from one strain to another like the example of what may be observed at the level of the immunological properties of the legionellas. Again, to these difficulties may be added those resulting from the non-selectivity likely to be observed due to 'parasite' hybridizations with DNA from other species which often accompany legionella in the environments in which they're found. On the other hand, it is the adaptation of this technique which will permit the development of a clean, selective and rapid method for the detection of L.P. in all the media likely to contain it, whether it be pathologic material or liquid or atmospheric samples, particularly waters or aerosols, volumes of any such mixtures found in installations implicated in the thermal exchange between liquids and the exterior atmosphere (air conditioning or heating systems), etc. The invention rests on the discovery that by using the whole genomes of *Legionella pneumophila* which have been fragmented by the restriction enzyme BamHI, then removing those restriction fragments which possess the BamHI ends (hereafter called "BamHI fragments") having sizes of the order of 20 kb and more preferable yet, those BamHI fragments whose sizes range from around 9.5 to 30 kb, and using the remaining fragments as the hybridizable material, probes may be obtained which permit practically universal detection of *Legionella pneumophila*, while however remaining selective in that the composition of the fragments thus obtained no longer lead to cross-hybridization reactions with the nucleic acids of microorganisms which often accompany legionellas in the media from which they may be isolated.

Consequently the invention concerns a process for the fabrication of a composition useable for the detection of legionellas, more particularly of *Legionella pneumophila*, a process characterized in that, starting from the total genomic DNA of a strain of *Legionella pneumophila*, it is fragmented by the action of the restriction enzyme BamHI, that from the mixture of BamHI fragments thus obtained, are removed principally those whose sizes are of the order of 20 kb, preferably as well as those whose sizes range between 9.5 and 30 kb and that the remaining mixture of fragments are collected, these fragments then constituting the aforesaid composition useable for the detection of legionellas.

This composition is advantageously labeled. All labels classically considered may be used. The composition may be labeled with the aid of radioactive tracers, or the DNA fragments contained in this composition may be modified by any chemical agent permitting, particularly after hybridization with the DNA sequences being sought, their detection by enzymatic, luminescent, fluorescent or other labels.

A preferred composition conforming to the invention is obtained from the L.P. strain which may be procured through the "American Type Culture Collection" (ATCC) under the no. ATCC 33 152.

Analogue conditions may however be obtained from a number of strains adequately grown (notably from strains whose ATCC numbers will be given further on) such that it may be reasonably inferred that an analogue composition may in fact be obtained from the genomic DNA from any strain of *Legionella pneumophila.*

The invention concerns more particularly yet, the compositions themselves of the fragments of the genomic DNA of *Legionella pneumophila,* useable for the selective detection of legionellas by hybridization with the genomic DNA extacted from legionellas or such DNA simply rendered accessible to hybridization, these compositions being constituted of a mixture of fragments of genomic DNA from *Legionella pneumophila,* more particularly characterized in that the mixture is essentially free of fragments themselves hybridizable both with, on the one hand, whole genomic DNAs of *Legionella pneumophila* such as the whole genomes from the strain ATCC 33 152 by treatment of these whole genomes with the restriction enzyme BamHI and subsequent separation of the BamHI fragments having different sizes.

The fragments having a size of the order of 20 kb apparently contain sequences which hybridize non-selectively with complementary sequences not only from legionellas but with those from genomic DNAs from other bacterial species and genuses. Such being the case, the selectivity is even further enchanced by taking the trouble to rid the mixture according to the invention, not only of the 20 kb BamHI fragments but also those whose sizes fall between around 9.5 kb and 39 kb.

In other words, the preferred compositions of the invention are formed of those BamHI fragments of the L.P. genome (preferably in its entirety initially) whose sizes are less than 9.5 kb or more than 30 kb respectively.

The definition which precedes supposes, in fact, that the mixture of fragments results practically exclusively from the treatment of the whole L.P. genome by the BamHI enzyme to the exclusion of any other method of fragmentation. However for some practical reason, the mixture could subsequently be subjected to other restriction enzymes, for example to obtain a mixture of smaller fragments (leaving aside the issue of the sometimes nearly inevitable mechanical cleavages). It may be readily seen, however, that the smaller fragments resulting from such supplementary treatment of the BamHI fragments which had been larger than 30 kb and now have sizes between 9.5 and 30 kb may be easily distinguished from the BamHI fragments of 9.5 to 30 kb as defined above in that they do not form (or at least not in substantial proportions) mutual hybrids under the appropriate conditions.

According to the case, only a part of the fragments resulting from the execution of the above-defined procedure are retained for the production of the probe compositions. In each case the specialist must weigh the possibility of increased selectivity from fewer fragments in the composition mixture against the reduced sensitivity which may result from the elimination of sequences which may be particularly effective to the hybridization, perhaps due to their highly repetitive nature in the L.P. genome.

The aforesaid operations for the separation of BamHI fragments or others may be performed by any of the known methods, as for example by gel-filtration, electrophoresis, or centrifugation through the appropriate gradients, all these methods obviously having in common the capacity to separate the DNA fragments according to their respective size.

The invention also concerns the detection methods themselves using the compositions conforming to the invention which have first been labeled (for example, radioactively) or rendered detectable or recognizable by molecules having an affinity or other products, themselves labeled or able to be labeled, notably after hybridization of at least certain of the fragments of the composition with the genomic DNAs of L.P. to be detected.

It is to be recalled that the essential operations of such detection are by preference the following:

deposition or attachment of the nucleic acids of the cells to be analyzed (or the cells themselves, first having been treated to render their nucleic acids accessible) on to an appropriate support, such as a filter of nitrocellulose, of nylon polyacrylamide or analogue;

putting the nucleic acids so attached or rendered accessible, into contact with the composition of DNA fragments according to the invention, under conditions permitting effective hybridization - if DNAs from legionellas are present;

elimination, notably by washing , of any non-hybridized fragments; and detection of labeled, hybridized fragments. As was said earlier, the detection could be by means of a radioactive tracer which has first been incorporated into the composition according to the invention. It may be preferable to use enzymatic, luminescent or fluorescent labeling. In which case it would be advantageous for the fragments of the composition to be previously chemically modified to introduce into them chemical groups which may later be coupled, directly or indirectly, with molecules having an affinity to them (notably to form complexes) or again with antibodies capable of recognizing these groups, these presenting the properties of a hapten or an antigen. For the conditions of such operations, reference may be made to the French Pats. No. 78 10975 or 81 24631 or again to European patent application No. 0063879.

Other characteristics of the invention will appear yet during the course of the description which follows the practical embodiments of the invention offered as non-limiting examples and the conditions under which the invention may effectively be put into operation.

The principle of the method according to the invention lies in the observation that the previously labeled L.P. DNAs hybridize in a relatively selective manner with the DNAs of legionellas, and more particularly of *L. pneumophila.* This selectivity is not however completely adequate. A certain amount of cross-hybridization between the DNAs of L.P. and other species which often accompany them in their natural envirionments, has been observed. To be sure the indications of hybridization are weaker when the DNA which has hybridized with the probe which is constituted from a whole L.P. genome, comes from another species. But understandably, such "noise" even at low levels could falsify or distort the measures and especially introduce a high risk of error in the case of samples containing relatively high proportions of 'foreign' bacteria relative to L.P. Among these other species may be mentioned the *enterobacteriaceae*, the *pseudomonaceae*, the *vibrionaceae*, and more particularly yet, the strain which were studied in the context of the experiments leading to this invention:

Acinetobacter calcoaceticus
Chromobacterium violaceum
Pseudomonas aeruginosa
Aeromonas hydrophila
Serratia fonticola
Enterobacter intermedium
Escherichia coli
Alcaligenes faecalis, etc..

The assays may be performed under the following conditions:

(1) Obtaining the DNAs from the bacteria under study

The DNA was prepared according to the technique described by D.J Brenner et al (Journal of Clinical Microbiology, 15, 1982).

(2) Fragmentation of the nucleic acids and recovery of the fragments
according to their respective sizes The purified DNAs obtained under the conditions of the preceding step were then treated by diverse restriction enzymes, more particularly BamHI and EcoRI, SamI, XhoI, etc..., according to the instructions of their respective manufacturers. After incubating overnight at ambient temperature (for SmaI) or at 37° C. (for the other enzymes), the reaction was stopped by heating the medium to 65° C. for 10 minutes.

Two methods were used to accomplish the aforementioned separations.

(a) Separation through a sucrose gradient

The DNA fragment solutions obtained from the preceding operation were subjected to separation by centrifugation through a 5–20% sucrose gradient after which the different fractions were collected. The fragment sizes in each fraction were verified by submitting an aliquot from each to electrophoresis on an agarose gel in the presence of size labels (in the present case, DNA from the phage, lambda, fragmented by the enzyme, HindIII). Those fractions having fragments smaller than 9,5 kb or larger than 30 kb were regrouped and dialyzed against a TE buffer (Tris 10mM, EDTA 1mM, pH 7.5). The DNA was precipitated and redissolved in a minimum volume of TE.

(b) Separation on an agarose gel

The fragments are separated by electrophoresis on an agarose gel.

The gel strips corresponding to the different fragment sizes to be separated are then cut apart. The DNAs contained in other parts of the gel are extracted from it by classic technique, for example by the method called the "freeze squeeze method" (compression sous congelation, in French) or by electrophoresis in a dialysis tube.

(3) Deposition of the study onto filters

The hybridizations were carried out on nitrocellulose filters (BA85 from Schleicher and Schull) or on nylon filters (Posidyne NAZ from Pall).

Deposition of the DNAs to be tested, onto the filters was accomplished essentially according to the techniques described by Grunstein and Hogness. The colonies were placed on filters, lysed in situ with a solution of sodium hydroxide 0.5N/NaCl 2.5N for 10 minutes at ambient temperature then neutralized with a sodium acetate solution, pH5. The filters were then dried at 80° C. for 2 hours.

(4) Hybridization

The filters are then pre-treated, or "pre-hybridized", with a solution of 100micrograms/ml of denatured herring sperm DNA at 67° C. for 1 hour in a medium of $2 \times NaCl/Cit/5 \times FPG$ and for another hour in a medium of $2 \times NaCl/Cit$; $1 \times FPG$; $KH_2PO_4$ 25mM; EDTA 2mM; sodium dodecylsulfate (SDS) at 0.5% by weight and dextran sulfate at 10% by weight. In what precedes: $1 \times FPG$ represents a solution containing 0.02% of a wetting agent called "Ficoll 400"; 0.002% polyvinyl pyrrolidone 350 (to avoid parasitic absorption of DNA); and Cit represents a solution of NaCl 0.15 M and sodium citrate 0.015 M.

Next is added the composition of radioactive DNA serving as a probe (having an activity of the order of $5 \times 10^7$ cpm/microgram) previously denatured by treatment at 100° C. for 5 minutes followed by rapid chilling. The hybridization then takes place during the night (around 17 hours at 67° C.). The filters are then washed several times, the last at 67° C., for 20 minutes each time in a solution 0.1 SSS; SDS at 0.1%. The filters are then autoradiographed on a Kodak X-omat intensification screen using Kodak X AR-5 films.

The systematic analysis of the DNA fragments obtained from legionellas, and more particularly from Legionella pneumophila, as well as from the other strains mentioned above has lead to the conclusion that the elimination of the BamHI fragments having sizes of the order of 20 kb had the effect of suppressing the cross-hybridizations which could be observed between legionellas and other strains.

The selectivity has manifested itself particularly effective in the analyses of the species *Legionella pneumophila*. As indicated above, it is particularly advantageous to use compositions of DNA fragmented by the restriction enzyme BamHI rid of the fragments having sizes between 9.5 and 30 kb and more particularly of the gel bands (major) corresponding to the sizes 21.4 and 16.2 kb and of the bands (minor) of 28, 12.8 and 10 kb.

What follows is the description of a preferred mode of execution of the procedures for the isolation and detection of legionellas. The water sample to be tested (1 liter generally) is filtered through a polycarbonate membrane of 0.2 micronpore size. After filtration, the membrane is placed, filtering side up, on a filter paper saturated with an acid buffer (PH 2.2) for 10 minutes, then blotted quickly on a dry filter paper and placed on a third filter paper saturated with a neutral buffer. After neutralization, the filter is place on a petri dish containing a selective nutritive gel medium and incubated at 37° C. for a variable time (in general, overnight). After this treatment, which aims to kill non-legionella microorganisms, the residues remaining on the filter are suspended in a small volume of distilled water (a few milliliters) and this suspension is centrifuged for 10 minutes at 10,000 g in a centrifuge of the EPPENDORF type. The supernatant is discarded and the proteins present in the pellet are extracted (treatment with sodium hydroxide 0.5 N for 10 minutes, neutralization with hydrochloric acid and Tris buffer, 3 extractions with phenol and 3 extractions with ethylether). A clear solution containing essentially the nucleic acids is thus obtained.

This solution is partitioned into as many aliquots as tests desired. After denaturation of the DNA by heat (100° C., 5 minutes, rapid chilling in ice), each aliquot is filtered through a nitrocellulose filter of 0.45 porosity using a "Hybri-dot" type filter apparatus. Each aliquot gives a "spot" of DNA of around 3 millimeters in diameter. The filter is heat treated at 80° C. for 2 hours and each spot cut out with hole-punch or paper-punch of the appropriate diameter, for example, 5–7 mm.Each little circle is hybridized with the probe conforming to the invention. After hybridization and removal of any unattached probe (by the usual methods), detection is carried out directly on the filter paper for the presence or absence of the labeled probe, either by auto-radiography or any other method corresponding to the nature of the label, enzyme for example.

Reference was made above to earlier patents in which non-radioactive labeling procedures were discussed. It is particularly advantageous to use probes labeled with an N-acetoxy-N-2-acetylaminofluorene (AAF) whose attachment to the DNA compositions may be effected essentially according to the techniques described in French patent no. 81 24631 which was identified above. In this latter case, the presence of *Legionella pneumophila* is expressed by the revelation of a colored spot after the detection of the DNA-AAF probe, particularly when anti-AAF antibodies are used, as described in the above-mentioned patent, themselves then being recognized by a second category of antibodies on which an enzyme is attached which has the characteristic of modifying the color of a specific substrate.

The process just described has permitted the selective recognition notably of the DNAs of the following strains (to cite only some examples):

L. pneumophila serogroup 1 - ATCC 33152,
L. bozemanii - ATCC 33217,
L. longbeachae serogroup 1 - ATCC 33462,
L. micdadei - ATCC 33204,
L. wadworthi - ATTC 33877,
L. oakridgensis - ATCC 33761,
L. jordanis - ATCC 33623,
L. feelei - ATCC 35072.

The above process is highly sensitive and so allows for the treatment of large volumes of water having low levels of microorganisms. This process is particularly advantageous because of its great sensitivity and its rapidity. In fact, it is possible to detect fewer than 300 picograms of the DNA of the bacteria being sought, that is, less than 100,000 individual bacteria in total. By way of comparison, current immunological methods require the accumulation of colonies visible to the naked eye which would number in several millions of bacteria and would require 4 to 6 days of culture.

To the contrary, the process according to the invention allows for legionella detection in less than 24 hours once the water to be tested contains over 100,000 bacteria per liter.

It has also been noted that those BamHI fragments removed from the DNA compositions conforming to the invention have the specific property of hybridizing with the ribosomal RNAs of legionellas and other species, particularly with *E. Coli* and more specifically with the 16S and 23S RNAs. Such ribosomal RNAs are sold by Boehringer, Mannheim, W. Germany). The composition of the DNA according to the invention then may again be defined as being constituted of a mixture of fragments of genomic DNA from *Legionella pneumophila* from which have been removed essentially all those DNA sequences which, in the genome, are susceptible to being transcribed into these ribosomal RNAs.

The invention thus concerns again as a variant, a procedure for the preparation of DNA compositions according to the invention characterized in that the total genomic DNA of L.P. is fragmented with restriction enzyme, notably BamHI, or by any other means and that those fragments which hypridize with the ribosomal RNA of *E. Coli* or L.P. are removed and that the other, non-hybridized fragments are collected.

To hybridize this operation, it is advantageous to have recourse to affinity chromatography columns using activated agarose, of the activated sepharose type, for example that sold under the name Sepharose 6MB. It is known that the nucleic acids may be attached to activated agaroses, notably by the contact of these latter with a solution of the nucleic acids to be attached, within a buffer also recommended by the manufacturer of the said activated agaroses.

The invention more generally yet concerns probes for the selective detection of species and even specified genuses of bacteria. These probes are characterized in that they are constituted of mixtures of fragments of genomic DNAs of the bacterial genus under consideration, having the capacity to hydridize with compositions of DNAs originating from the said genus, or with the bacteria themselves once their DNAs have been rendered accessible to such hybridization, this mixture being, however, essentially free of fragments which are themselves hybridizable with both (a) whole genomic DNAs originating from bacteria of the same genus, and (b) with fragments of DNAs equally hybridizable with the aforesaid genomic DNAs, but hybrizable also with DNAs coming from bacteria of a different species or genus.

The compositions preferred for the selective detection of bacteria of the genus under consideration are free of genomic DNA sequences susceptible to be transcribed to ribosomal RNA. The particular compositions preferred are those which are assentially exempt from sequences of genomic DNA which hybridizes with the 16S and or 23S ribosomal RNAs of *E. coli.*

The possibility of using, as a selective probe for the detection of bacteria belonging to a specific genus or species, compositions of DNA fragments containing the major part of the genomic DNA of bacteria of the genus or species considered, to the exclusion of a minor proportion of certain sequences only, is an altogether remarkable result.

The expression "mixture essentially exempt" nevertheless does not exclude that the compositions according to the invention might still contain certain sequences, at once non-repetitive and non-selective, as long as they don't interfere in any essential manner with the sensitivity and selectivity of the detection of DNA sequences characteristic of the genus or of the species considered, present in predominant proportions.In particular, the signal furnished by the predominant sequences is much stronger than that given by any non-selective minority sequences which may still be present, so that the rigor of the detection may be assured. It goes without saying that the expression "signal" corresponds to the nature of the phenomenon used for the selective detection, for example radio activity, action on an enzymetic substrate,etc. of the label carried by the composition used as a probe.

The invention also concerns a process to prepare a DNA composition utilizable as a specific probe for the detection of bacteria of a given genus.

This process includes essentially the steps which will be described hereafter. The raw material for the preparation of such a composition consists of the total genomic DNA of a bacteria belonging to the genus in consideration. This bacteria preferably corresponds to that whose detection is being sought. For example, it belongs to a given species or sub-species. In what preceded, this bacteria, hereafter referred to as the "reference bacteria" belonged to the species *Legionella pneumophila*.

The first step consists in the isolation of the DNAs belonging to the genuses of bacteria which, in nature, often accompany those bacteria of the genus to be detected. Examples of bacterial genuses often encountered along with legionellas were recalled above. Then these total genomic DNAs are deposited on an appropriate support, notably of nitrocellulose or nylon, under the classical conditions for hybridization operations. Next, the possibility of hybridization is allowed between the total genomic DNA obtained from the reference bacteria and the total genomic DNAs belonging to the other genuses retained for the assay.

To the extent that the total genomic DNA contains substantial proportions of non-selective sequences in common with sequences contained in certain at least of the total genomic DNAs of the other bacteria, a positive hybridization is observed between the total genomic DNA of the reference bacteria and the total genomic DNA of at least one of the other bacteria, for example one which will be designated hereafter, for the purposes of this presentation, by the expression "bacteria 1".

The second step of the process according to the invention then includes the formation of preparations by digestion of the total genomic DNA of the reference bacteria, respectively by the various restriction enzymes, for example the enzymes BamHI, EcoRI, HindIII, HpaI, PvuII, SmaI, XhoI, etc., and, for each of the preparations, the separation according to size, of the fragments of DNA resulting from the digestion by the corresponding restriction enzyme, for example by electrophoresis of the fragments on an appropriate gel, and the transfer of the fragments now separated one from the other, on to a hybridization support, for example by Southern's well-known method.

The next part of this process then consists of the hybridization assays of the reference fragments thus isolated from each other, from each of the enzyme preparations, with the total genomic DNA of "bacteria 1".

The following observations may then be made at the level of each of the preparations of genomic DNA from the reference bacteria. In the case of certain preparations, hybridizations implicating a great number of different sized fragments may be observed on the hybridization filter. In the case where the genomic DNA of "bacteria 1" had been radioactively labelled, any radioactivity retained on the filter will be photographically detected as "smears" (or elongated blobs of contrast). This observation generally represents the presence of highly repetitive sequences both in the genomic DNA of the reference bacteria as well as in the genomic DNA of "bacteria 1". Such observations lead to the rejection of the preparations in question.

While, on the contrary, the observation for other preparations of hybridizations localized only at the level of one or a limited number of DNA fractions on the nitrocellulose filter with the reference DNA bears witness, instead, of the selectivity of these other fractions separated from the genomic DNA of "bacteria 1".

It was, for example, just this sort of observation which occurred when this technique was applied to the DNAs of L.P., and on a preparation which had been previously digested by the enzyme BamHI.

Starting from a preparation of the total genomic DNA of the reference bacteria, in order to obtain a mixture of DNAs from the reference bacteria which no longer hybridize with the total genomic DNA of "bacteria 1", one need only digest the total genomic DNA of the reference bacteria with the corresponding restriction enzyme as the test composition (for example BamHI in the case of L.P.) and eliminating fragments whose sizes correspond to those which, in the above-indicated hybridization assay, hybridize with the DNA of "bacteria 1". Thus may be obtained a mixture of fragments of DNA from the reference bacteria which already permits the selective detection of the reference bacteria relative to "bacteria 1".

The third step of the process according to the invention then consists of repeating the hybridization assay of the aforesaid first step, of the mixture of fragments of genomic DNAs originating from the reference bacteria, those fragments which hybridize with the DNA of "bacteria 1" being removed, and obtained at the end of the second step, with the ensemble of the total genomic DNAs of the "collateral" bacteria initially singled out in the operation of the first step of this procedure. The possible observation of a new non-selective hybridization with the total genomic DNA of, for example, a "bacteria 2" would lead the experimenter to repeat the cycle of selection operations set forth in the second step indicated above, but this time carrying out the hybridization assays between the total genomic DNA of "bacteria 2" and the preparations of DNA fragments of different sizes obtained from the digestions by the respectively distinct restriction enzymes, from the reference bacteria. Thus may be obtained all over again the mixtures of DNAs issued from the reference bacteria, which are selective relative to "bacteria 2", after treatment of the total genomic DNA of the reference bacteria by the appropriate restriction enzyme and removal of those fragments hybridizing with the genomic DNA of "bacteria 2".

It may be noted that the DNA sequences in common between the reference bacteria and the "bacteria 1" at least partly coincide with the sequences in common between the total DNA of the reference bacteria and the DNA of "bacteria 2". The elimination of all such sequences in common from the total genomic DNA of the reference bacteria leads then to a mixture of DNAs originating from the reference bacteria which no longer hybridize with the DNA of either "bacteria 1" or "bacteria 2".

As an alternative, a similar composition may be obtained which no longer hybridizes with either "bacteria 1" or "bacteria 2", by using for the hybridization assays of the aforesaid second cycle, the mixture of fragments obtained from the total genome of the reference bacteria but after removal of the sequences which hybridize with the DNA of "bacteria 1", instead of the total genome.

Theoretically, the preceding operations could be repeated with the total genomic DNA of a "bacteria3". But experience has shown that in general such experiments need not be repeated more than once or twice. In fact, it should not be forgotten that if bacteria of different genuses may contain a certain number of sequences in common, for example those coding for ribosomal RNAs, they are generally characterized by major sequences of DNA which are unique to them. In addition, it is mostly a matter of eliminating those sequences which are often repeated in the bacterial genome. The odd gene, perhaps in common, cannot in fact lead to significant 'signals' in the selective hybridization assays. They are minor in number relative to those sequences which are genuinely selective, once the said repetitive sequences have been removed from such DNA mixtures. And there aren't a great many repetitive sequences in the bacteria. They are constituted essentially of sequences coding for ribosomal RNAs and the transposons.

In what has preceded, essentially what was discussed was the application of these techniques for the preparation of compositions utilizable as probes for the selective detection of bacteria belonging to a given genus. It goes without saying that this technique may be extended if necessary, to produce DNA preparations which permit selective detection of a particular species of bacteria within a given genus.

The techniques just described and which were,naturally, used in the development of DNA compositions for the selective detection of L.P., are just as useable under the same sorts of conditions for the selective detection of totally different bacterial genuses or species.

To mention only a few examples of the possibility of the application of this process under similar conditions, to the selective detection of bacteria belonging to phylogenetically distinct taxonomic groups, consider: Brucella, Campylobacter, Bordetella, Acinetobacter, *Haemophylus ducreyi,* etc..

In one variant of the process which has been described above, in the second step a hybridization of the preparations fragmented according to their sizes and transferred onto a filter, could equally be undertaken with the ribosomal RNAs of E. coli, for example those which were identified above. After elimination of those fragments which hybridize with these ribosomal RNAs, from a preparation of DNAs which has been digested by an appropriate restriction enzyme, preparations whose selectivity may then be tested anew under the conditions defined in the aforesaid third step are obtained. If the case applies, the process according to the invention may be repeated under the conditions described in the first, second and third steps, if the elimination of the sequences hybridizing with ribosomal RNAs is not sufficient to assure the achievement of preparations of DNAs sufficiently selective for the practically certain detection of bacteria of the genus or species in question. It should be noted that the ribosomal RNAs of other bacteria than the E. coli could be used. However it should be remembered that great homologies exist between the ribosomal RNAs of different bacterial species. These ribosomal RNAs are in fact characterized by the marked sequence stability over the course of phylogenetic evolution (or what is commonly called the evolution of living beings).

The invention is of a general nature relative to the ensemble of bacterial species. In its principle, which is the elimination of sequences which could lead to troublesome cross-hybridization, it could be applied to the selective detection of other microorganisms, notably of viruses.

For example, a composition utilizable as a probe for the detection of Brucellas may be obtained by treating a composition of DNA from Brucella under experimental conditions like those described relative to *Legionella pneumophila,* but replacing the enzyme BamHI used for the restriction, with KpnI, and by separating from the fragment composition obtained, those KpnI fragments of 6.5kb which hybridize with the ribosomal RNAs of the Brucellas as well as of *E. coli,* in particular with the 16S and 23S RNAs mentioned above.

Essentially the following conditions applied:

Starting from a composition constituted of DNAs from *Brucella melitensis* biovar 1, strain reference "16 M" (BCCN R 1; ATCC 23456), it is treated with enzyme KpnI and , after fragmentation, DNA fragments of 6.5kb corresponding to genes coding for 16S and 23S RNAs are separated out by centrifugation through a sucrose gradient or by electrophoresis on agarose. The composition then utilized as a "probe composition" is consequently constituted of the ensemble of DNA fragments having a molecular weight either inferior or superior to around 6.5 kb, after being labelled under the conditions indicated above. In this assay, the probe was labelled by 'nick translation' with $^{32}P$. The probe has already been tested in hybridization assays with DNAs from Flavobacterium, Xaothomonas, Yersinia, Serratia, E.coli, Pseudomoniae, Enterobacter, Proteus, Salmonella, Citrobacter, Haquia, Actinobacillus, Pasteurella, Listerella, Haemophilus, Brucella, Acinetobacter, Legionella, and Aeromonas, deposited on nylon filters (Amersham and Pall) in 'spots' of 0.3μg. Hybridization reactions were observed only with Brucella.

This invention is in on way limited to those applications or embodiments herein particularly described, but on the contrary embraces all variants.

We claim:

1. A composition for detecting a microorganism of the genus Leqionella, wherein the composition comprises:

a mixture of BamHI DNA fragments of Leqionella pneumophila, wherein the fragments are capable of hybridizing with DNA originating from a Leqionella microorganism;

and wherein said mixture is substantially free of DNA fragments hybridizable with whole genomic DNA of *Leqionella pneumophila;* and further wherein said mixture is substantially free of BamHI fragments having sizes of about 20kb, wherein said BamHI fragments correspond to fragments from the whole genome of *Leqionella pneumophila* by treatment of the whole genome with the restriction enzyme BamHI.

2. The composition of claim 1, wherein the BamHI fragments are derived from the genome of *Leqionella pneumophila* having the identifying characteristics of ATCC 33152.

3. The composition of claim 1, wherein said mixture consists essentially of BamHI fragments having sizes greater than about 50kb.

4. The composition of claim 1, wherein said mixture is substantially free of DNA sequences that are capable of hybridizing with 16S ribosomal RNA and 23S ribosomal RNA of E. coli.

5. The composition of claim 1, wherein DNA fragments in said mixture are labeled.

6. A composition for detecting a microorganism of the genus Leqionella, wherein the composition comprises:

a mixture of BamHI DNA fragments of *Legionella pneumophila,* wherein the fragments are capable of hybridizing with DNA originating from a Leqionella microorganism;

and wherein said mixture is substantially free of DNA fragments hybridizable with whole genomic DNA of *Leqionella pneumophila;* and further wherein said mixture is substantially free of BamHI fragments having sizes of about 9.5kb to about 30kb, wherein said BamHI fragments correspond to fragments from the whole genome of *Leqionella pneumophila* by treatment of the whole genome with the restriction enzyme BamHI.

7. The composition of claim 6, wherein the BamHI fragments are derived from the genome of *Leqionella pneumophila* having the identifying characteristics of ATCC 33152.

8. The composition of claim 6, wherein said mixture consists essentially of BamHI fragments having sizes greater than about 50kb.

9. The composition of claim 6, wherein said mixture is substantially free of DNA sequences that are capable of hybridizing with 16S ribosomal RNA and 23S ribosomal RNA of E. coli.

10. The composition of claim 6, wherein DNA fragments in said mixture are labeled.

11. A composition for detecting a microorganism of the genus Leqionella, wherein the composition comprises:

a mixture of BamHI DNA fragments of *Legionella pneumophila,* wherein the fragments are capable of hybridizing with DNA originating from a Leqionella microorganism;

and wherein said mixture is substantially free of DNA fragments hybridizable with whole genomic DNA of *Leqionella pneumophila;* and further wherein said mixture is substantially free of BamHI fragments capable of hybridizing with ribosomal RNA of Leqionella and *Escherichia coli,* and said BamHI fragments correspond to fragments from the whole genome of *Leqionella pneumophila* by treatment of the whole genome with the restriction enzyme BamHI.

12. The composition of claim 11, wherein said mixture is substantially free of DNA fragments hybridizable with 16S and 23S ribosomal RNA of *Escherichia coli.*

13. The composition of claim 11, wherein DNA fragments in said mixture are labeled.

14. A process for preparing a composition for detecting a microorganism of the genus Leqionella, wherein the process comprises:

providing whole genomic DNA from *Leqionella pneumophila;* treating said whole genomic DNA with the restriction enzyme BamHI to form a DNA digest containing a multiplicity of BamHI fragments; and separating BamHI fragments having sizes of about 20kb from said digest.

15. The process of claim 14, which further comprises labeling BamHI fragments in said composition with a label selected from the group consisting of radioactive, enzymatic, luminescent, and fluorescent labels.

16. The process of claim 14, wherein said composition consists essentially of BamHI fragments having sizes greater than about 50kb.

17. A process for preparing a composition for detecting a microorganism of the genus Leqionella, wherein the process comprises:

providing whole genomic DNA from *Leqionella pneumophila;* treating said whole genomic DNA with the restriction enzyme BamHI to form a DNA digest containing a multiplicity of BamHI fragments; and separating BamHI fragments having sizes of about 9.5kb to about 30kb from said digest.

18. The process of claim 17, which further comprises labeling BamHI fragments in said composition with a label selected from the group consisting of radioactive, enzymatic, luminescent, and fluorescent labels.

19. A process for preparing a composition for detecting a microorganism of the genus Leqionella, wherein the process comprises:

providing whole genomic DNA from *Leqionella pneumophila;* treating said whole genomic DNA with the restriction enzyme BamHI to form a DNA digest containing a multiplicity of BamHI fragments; and separating BamHI fragments capable of hybridizing with ribosomal RNA of Leqionella and *Escherichia coli* from said digest.

20. The process of claim 19, wherein DNA fragments hybridizable with 16S and 23S ribosomal RNA of Escherichia coli are removed from said digest.

21. The process of claim 19, which further comprises labeling BamHI fragments in said composition with a label selected from the group consisting of radioactive, enzymatic, luminescent, and fluorescent labels.

* * * * *